United States Patent
Sotiropoulos et al.

(10) Patent No.: US 6,364,871 B1
(45) Date of Patent: Apr. 2, 2002

(54) METHOD AND DEVICE FOR SCULPTURING LASER BEAMS

(75) Inventors: Nicholas Sotiropoulos, Glen Mills; Gregory Berlin, West Chester, both of PA (US); George Rozakis, North Olmsted, OH (US)

(73) Assignee: Apollo Vision, Inc., Glen Mills, PA (US)

(*) Notice: Subject to any disclaimer, the term of this patent is extended or adjusted under 35 U.S.C. 154(b) by 0 days.

(21) Appl. No.: 09/284,842
(22) PCT Filed: Oct. 21, 1997
(86) PCT No.: PCT/US97/19081
    § 371 Date: Jul. 14, 1999
    § 102(e) Date: Jul. 14, 1999
(87) PCT Pub. No.: WO98/17181
    PCT Pub. Date: Apr. 30, 1998

Related U.S. Application Data
(60) Provisional application No. 60/028,773, filed on Oct. 21, 1996.

(51) Int. Cl.$^7$ ................................................ A61B 17/00
(52) U.S. Cl. ................................................ 606/5; 606/4
(58) Field of Search ................................ 606/1, 4, 5, 11, 606/12

(56) References Cited

U.S. PATENT DOCUMENTS

| | | | | |
|---|---|---|---|---|
| 4,941,093 A | * | 7/1990 | Marshall et al. | 606/5 |
| 5,395,356 A | * | 3/1995 | King et al. | 606/4 |
| 5,411,501 A | * | 5/1995 | Klopotek | 606/4 |
| 5,642,287 A | * | 6/1997 | Sotiropoulos et al. | 606/5 |
| 5,713,892 A | * | 2/1998 | Shimmick | 606/5 |
| 5,807,379 A | * | 9/1998 | L-Esperance, Jr. | 606/5 |

FOREIGN PATENT DOCUMENTS

| EP | 628298 | * 12/1994 | 606/5 |
|---|---|---|---|

* cited by examiner

Primary Examiner—Michael Buiz
Assistant Examiner—Julian W. Woo
(74) Attorney, Agent, or Firm—Synnestvedt & Lechner LLP (57) ABSTRACT

This invention is a method for sculpturing a laser beam (13) in a predetermined pattern using a device (17) between the laser source (11) and the target (23). The method comprises a series of sequential steps in which at least two regions of the cornea (177) are each exposed to increasingly larger portions of the laser beam (13). In the preferred embodiment, two pairs of complementary regions of the cornea (177) will be sequentially exposed to laser radiation. In each such region, a first part will be exposed to a substantially segmental portion of the beam (13), and then at least another larger substantially segmental portion of the beam (13) in which the larger segmental portion, includes the smaller segmental portion. In the preferred embodiment, the target (23) is the human eye, and the predetermined pattern is intended to shape the eye to treat it for astigmatism, myopia, or hyperopia.

5 Claims, 8 Drawing Sheets

METHOD AND DEVICE FOR SCULPTURING LASER BEAMS

This application claims benefit to U.S. Provisional application 60/028,773 filed Jan. 2, 1996 also this application is a 371 of PCT/US97/19081 filed Oct. 21, 1997.

FIELD OF THE INVENTION

The present invention relates to systems, methods and devices for sculpturing a laser beam. More particularly, the invention relates to a device located in the path of a laser for blocking or occluding a portion of the laser beam in accordance with a predetermined pattern wherein the portion of the laser beam reaching the target may be varied, and to methods for using such a device. The use of lasers to alter the surface of objects is becoming more important as it becomes apparent that lasers may be precisely focused and the amount of energy transferred to the target can be closely controlled. Lasers have been used in eye surgery, for example, to treat the retinae of diabetic persons. Lasers have also been used by doctors for other precise and delicate eye surgery.

In all of the prior art eye surgery procedures, as well as in other efforts to use laser beam pulses to act on or burn away tissue or other matter, a great concern arises about the ability to control the size and intensity of the beam. In addition, when multiple treatment pulses are intended, precise location and shaping of the beam is desirable.

BACKGROUND OF THE INVENTION

Until recently, it has not been possible to provide a practical predetermined pattern of treatment where the intensity and duration of the laser pulse is controlled while simultaneously controlling the shape of the laser pulse and the location where the pulse strikes the target. It has been found that the cornea of the eye may be shaped or otherwise treated with a laser beam pulse in a plurality of locations on the eye to achieve a desired result. Until now, however, the ability to control the size, shape and location of the beam has been undesirably limited. It has recently been discovered that predetermined control of the laser beam pulse may be accomplished by passing the laser beam through an iris that is centered on both the axis of the laser beam and on the optical axis of the cornea. By controlling the size of the iris opening and simultaneously controlling the amount of laser energy passing through the iris aperture, the surface curvature of the eye can be changed to correct for myopia or near sightedness. Such a procedure, however, has not found widespread acceptance due to inherent limitations in beam shape and size that an aperture of this type provides. For example, the use of an iris only permits a round, symmetrical alteration in laser beam shape that is not useful for treatment of astigmatism, hyperopia, irregular shapes and even repair of over corrected or inaccurate corrections for myopia.

Treatment for hyperopia by means of a laser necessarily involves the removal of more corneal tissue at the periphery as compared to the center region of the cornea. As a result, the use of only a variable iris-type aperture to alter the shape of a laser beam cannot accomplish this purpose. Teachings in the prior art, such as Yoder, Jr. U.S. Pat. No. 5,219,344, disclose the use of annuli of varying size to effect a greater exposure of peripheral corneal tissue. Notably, however, the methods and apparatus described in Yoder, Jr. also inherently require the use of shapes that are symmetrical about the axis of the laser beam and about the optical axis of the cornea. These methods are therefore inherently limited by the use of aperture discs having a limited number of annuli. Further, the inability to vary the shape of such annuli imposes additional limitations upon the operator as this inability limits the extent to which the cross-sectional shape of the laser beam can be modified.

Similarly, Trokel U.S. Pat. No. 5,108,388 describes a laser surgery method which employs masks having limited numbers of circular or slit-shaped apertures. The inherent limitations in such a method is similar to that of Yoder, Jr. More specifically, while Trokel teaches that any suitable number of openings can be formed in the masks, the cross-sectional shape of the laser beam is nonetheless limited by the specific openings so provided. As a result, the flexibility desired in treating any given curvature malformation or combination of curvature malformations cannot be achieved.

In a more telling example of the limitations of the prior art, the treatment of hyperopia combined with an astigmatism presents an even further complicated problem as tissue not only from the periphery but also along the major axis of the astigmatism must by preferentially removed compared with other regions of the cornea. The methods and apparatus of Yoder, Jr. have significant disadvantages when applied to such a procedure as two different aperture discs, one applicable to hyperopia and one applicable to astigmatism, must be used in conjunction. More importantly, and as above, the aperture discs contain a limited number of apertures from which to select in shaping the cross-sectional area of the laser beam applied to the cornea. As a result, to the extent the procedure can even be performed by the methods and apparatus of Yoder, Jr., inferior results are inevitably obtained.

The teachings of Shimmick, et al. U.S. Pat. No. 5,549,597, while overcoming certain of the disadvantages of Yoder, Jr., is limited in its applicability. Shimmick, et al., which applicants note is not necessarily prior art to the present invention, teaches a device which has variable cylinder blades which are useful in the treatment of astigmatisms. This usefulness is limited, however, as the operation of the cylinder blades cannot provide an effective treatment of hyperopia or an astigmatism combined with hyperopia. Moreover, insofar as the teachings of Shimmick, et al. are silent with respect to either independent movement of the cylinder blades or movement of the cylinder blades asymmetric to the center line of the iris, it fails to overcome many of the limitations found in the prior art.

OBJECTS OF THE INVENTION

In view of the deficiencies and disadvantages of the prior art as recognized by applicants, it is an object of the present invention to provide a system, method and device for sculpturing the shape of a laser beam to change the shape of the beam that impacts its intended target.

Another object of this invention is to provide a system, method and device which is useful in sculpturing laser beams into asymmetrical laser beam subportions, including shapes that are not round.

Yet another object of the present invention is to provide a system, method and device capable of shaping a laser beam to permit treatment of astigmatism, hyperopia, irregular shapes and even repair of over corrected or inaccurate corrections for myopia.

SUMMARY OF THE INVENTION

It has been unexpectedly found that the systems, methods and devices of the present invention overcome the limitations of the prior art, without adding unnecessary complexity. More specifically, applicants have found that it superior results in the shaping of a cornea can be achieved by using methods and devices which expose a plurality of corneal regions to a plurality of asymmetrical laser beam subportions to affect the shape of said cornea without introducing any substantial asymmetry to the shape of said cornea. Thus, applicants have discovered that by abandoning the teachings of the prior art which rely on laser beam shapes that are substantially symmetrical about the laser beam axis, methods and devices of substantially superior flexibility, economy and practicality can be realized. Accordingly, preferred method aspects of the present invention comprise providing a laser beam having an predefined shape along a beam axis and exposing a plurality of corneal regions to a plurality of asymmetrical laser beam subportions to affect the shape of said cornea without introducing any substantial asymmetry to the shape of said cornea. As used herein, the term "asymmetrical laser beam subportions" refers to portions of the laser beam which are not symmetrical about the axis of the laser beam. According to preferred embodiments, the cross sectional shape of the laser beam subportion is substantially defined by a portion of the periphery of said predefined shape, with each of said subportions of said laser beam being produced by occluding a portion of said beam of predefined shape.

A preferred device according to the present invention comprises means for producing a plurality of asymmetrical laser beam subportions from a laser beam traveling along a laser beam axis. Applicants have found that by the use, for example, of a single plate movable in all directions across the path of the laser beam, or a plurality of plates independently operable across the path of the laser beam, the ability to occlude a laser beam to achieve a nearly infinite variety of laser beam subportions can be achieved. An operator of the device can thus occlude the beam to produce a series of laser beam subportions that are highly desirably in the treatment of any curvature malformation or combination of curvature malformations. As a result, the desired corneal curvature can be achieved simply and efficiently, as explained in more detail hereinafter.

The preferred system includes a laser source for directing a laser beam along a laser axis and a target for receiving the laser beam. The device of this invention is located in the laser beam path such that the device is aligned such that any chosen portion of the laser beam is obstructed or occluded.

In a preferred embodiment, the target is the human eye and, more particularly, the cornea of a human eye. The predetermined pattern is intended to shape the cornea as the laser contacts it in controlled pulses at predetermined locations on the cornea, preferably to treat astigmatism, myopia, or hyperopia.

The methods of the present invention comprise a series of sequential steps in which at least two regions of the cornea are each exposed to increasingly larger portions of the laser beam. As the cross-sectional area of the beam is increased, the larger portion of the beam will be understood to include the preceding smaller portion as well thereby exposing the area of the cornea previously exposed to additional laser radiation. In this manner, the entire area of the cornea exposed to laser radiation will be shaped to the desired curvature by gradually varying the amount of exposure across the exposed area.

In the preferred embodiment, two pairs of complimentary regions of the cornea will be sequentially exposed to laser radiation. In each such region, a first part will be exposed to a substantially segmental portion of the beam, and then at least another part will be exposed to a larger substantially segmental portion of the beam in which the larger segmental portion includes the smaller segmental portion. It will be understood that a complementary region of the cornea comprises that region which, when added to the region to which it is complimentary, defines the entire corneal area exposed to laser radiation.

In a more preferred embodiment, each region of the cornea to be treated will be exposed to about forty substantially segmental portions in which each subsequent portion is larger than and includes each preceding portion. It will be understood that as used herein, a substantially segmental shape includes any shape defined by a substantially arcuate boundary and a substantially non-arcuate boundary and that the base of any such shape is understood to be the substantially non-arcuate boundary and the arc of any such shape is understood to be the substantially arcuate boundary. It will be further understood that the arcuate boundary of the beam can include a transition zone through which the cross-sectional area of the beam can expand incrementally from beam portion to beam portion thereby creating a gradual ablation of the periphery of the corneal region so exposed.

According to certain preferred embodiments, the device employed herein includes a housing and frame on which the components that occlude the laser beam are mounted. Control of the device may be accomplished manually but it is preferred that the various components be controlled by a computer into which the desired data has been entered. A keyboard and video monitor are also preferably used in the system to input data and to observe displays of various treatments being performed.

The device preferably includes an iris defining an aperture that is aligned perpendicularly with the axis of the laser beam and, even more preferably, an adjustable iris for adjustable movement of the aperture about the axis. When an adjustable iris is used, the iris is preferably controlled by controlling means receiving instructions from the operator or program of the computer for enlarging or shrinking the aperture as planned. The size of the iris aperture is preferably varied by a gear and electric motor assembly that permits accurate adjustment of the aperture dimension to within the needed tolerances.

Also included in the preferred device is a laser beam modifying means for producing a plurality of asymmetrical laser beam subportions from a laser beam traveling along a laser beam axis. According to preferred embodiments, the modifying means comprises at least one plate movable so as to further obstruct a portion of the laser beam that would otherwise pass through the iris. As used herein, a plate includes a door, gate, shutter or other similar structure which can obstruct or occlude the laser beam. Preferably, the beam modifying means includes a pair of opposed door sections. In one embodiment, the beam modifying means operates the pair of door sections symmetrically about the axis, preferably such that the symmetrical movement of the pair of door sections is simultaneous.

In a highly preferred embodiment, the beam modifying means operates the pair of door sections independently so as to permit movement of one section without regard to movement of the other section. This independent movement and control allows for substantially more flexibility in designing the shape, size and predetermined pattern of the laser beam. The beam modifying means preferably includes a motor for moving the door sections through gears that allow precise movement that is repeatable with respect to a fixed point in space such as the axis of the laser beam to provide maximum control and effectiveness of the present invention. In a preferred embodiment, each of two door sections are operated by a separate motor.

In an alternate preferred embodiment, the beam modifying means includes a single plate which is capable of obstructing any portion including the entirety of the laser beam. In this preferred embodiment, the beam modifying means preferably includes means for moving the plate into positions to occlude substantially any and all portions of the laser beam.

In the preferred embodiment in which the beam modifying means includes two independently movable door sections, the controlling means is also adapted to rotate the device about the laser axis so that the door sections are capable of intercepting any portion of the laser beam as desired. To accomplish this goal, a portion of the device is adapted to be rotated in both the clockwise and counter-clockwise directions so as to provide a full circle of laser beam interception or control. In the alternate preferred embodiment in which the beam modifying means includes a single plate, the controlling means need not but may be adapted to rotate the device about the laser axis as the single plate is preferably adapted to obstruct any and all portions of the laser beam without such rotation.

BRIEF DESCRIPTION OF THE DRAWINGS

For a more complete understanding of the invention, reference is hereby made to the drawings, in which:

FIG. 14 is a diagrammatic view of the exposures in a 90° rotation in a compressed from.

DETAILED DESCRIPTION OF PREFERRED EMBODIMENTS

The Systems and Devices

Figure 1:
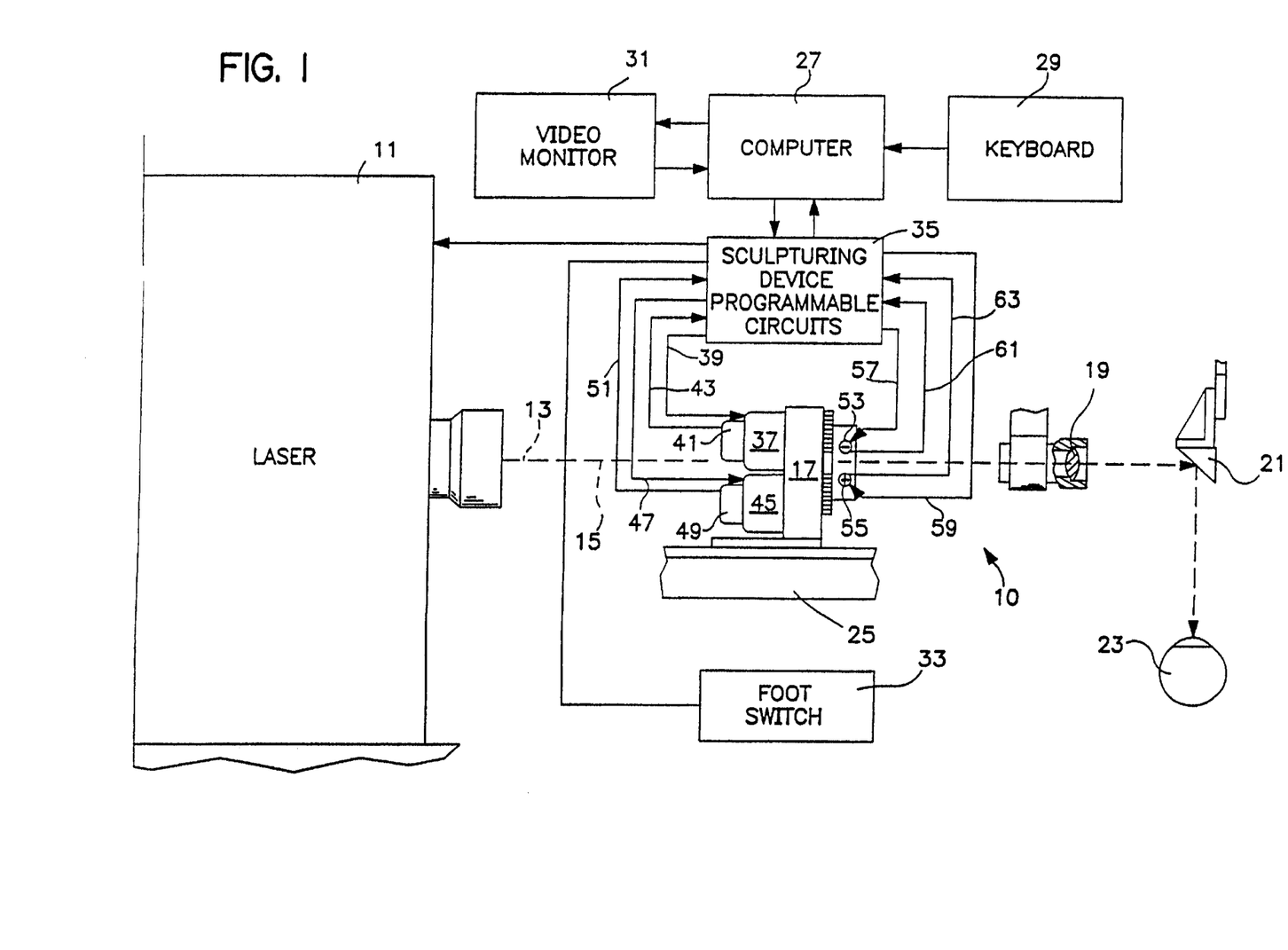
FIG. 1 is a schematic view illustrating the environment and operating components for the device of this invention as used in an eye corrective surgical procedure.

As shown in the drawings, a system for sculpturing a laser beam has been developed for control of the laser beam as it acts on the target for which it is intended. The system, generally at 10, includes a laser source 11 directing a laser beam source 13 along an axis 15 through the device of this invention, generally at 17, in which the laser beam is sculptured as described herein. The sculptured beam then passes through a focusing lens assembly 19, is directed by mirror 21, and reaches a target such as eye 23. Focusing lens assembly 19 and mirror 21 are used to align the laser beam properly with respect to the target once the system has been mounted on an appropriate table 25.

The device 17 is controlled by a computer 27 that has a circuit board installed within a computer, such as an IBM PC or an IBM compatible computer. The computer is programmed via keyboard 29 to provide a predetermined pattern of action by the laser, such as, for example, the laser pattern and number of laser pulses for a corneal surgery treatment to correct astigmatism, myopia, or hyperopia. The video monitor 31 allows the operator to review measured or programmed data and to observe displays of various treatments being performed.

The computer program provides instructions to the device 17 to operate four axes of motion. The laser beam is sculptured by passing the beam through the device 17 such that an iris aperture and preferably two doors intersect the beam in a predetermined pattern.

Foot activated switch 33 permits the operator to send activation signals to the system while retaining control over the patient by allowing the operator to position or adjust the target, such as the cornea of a human eye. With the pulsed laser beam, the target is sculptured each time according to the predetermined program, either from the computer software or from direct input from an operator. Note also that when the foot activated switch 33 is used, the operator is also free to use the keyboard 29 at any time. The system of this invention is capable of automated operation with the entire treatment regimen being programmed into the computer so that all that is needed is to position the patient and begin the operation. Alternatively, a doctor may choose to manually input each succeeding pulse or group of pulses of the laser depending upon the results of the preceding pulse or group of pulses.

Turning now to the device shown generally at 17 in FIG. 1, it can be seen that wires connect the device to the controlling means via computer 27 and circuit board 35 to control a first motor 37 via wire 39 and receive feedback from first encoder 41 via wire 43. Similarly second motor 45 receives input from wire 47 and second encoder 49 provides the needed feedback to computer 27 via wire 51. First and second motors 37 and 45 are mounted on what is described as the front of device 17, where the laser axis 15 enters the sculpturing device. On the back side of device 17 are a pair of motors 53 and 55, shown in FIGS. 2 and 3, that are controlled by input wires 57 and 59 respectively and provide feedback via wires 61 and 63 respectively.

Figure 4:
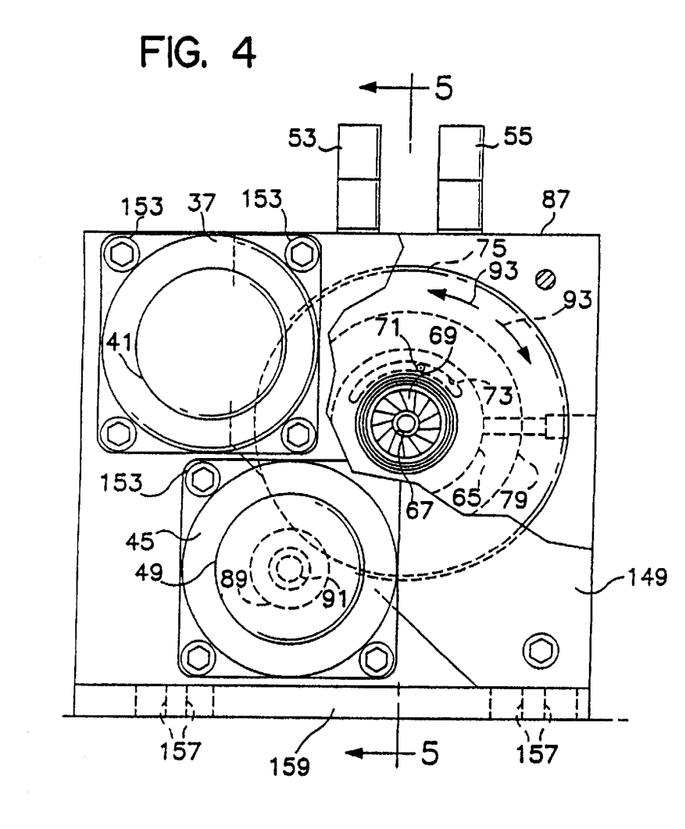
FIG. 4 is a front or left hand elevational view of FIG. 2 with a portion of a cover plate broken away to show certain details of the iris activating mechanism.
Figure 5:
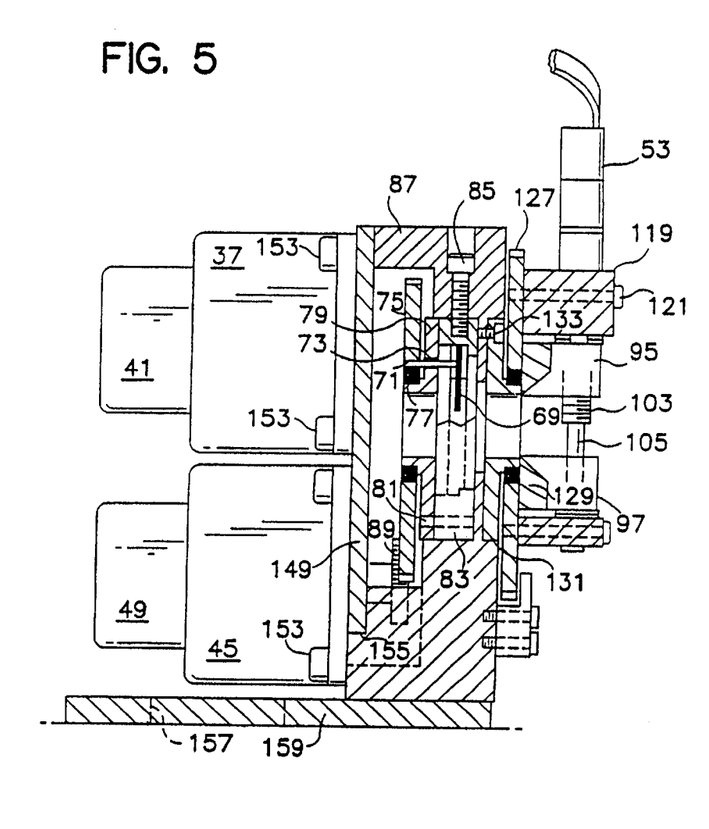
FIG. 5 is a sectional elevational view taken along the line 5,5 of FIG. 4, showing still more details of the iris activating mechanism and the mounting of the adjustable door and slot mechanism.

The sculpturing device 17 includes an iris 65 shown in FIG. 4 with an aperture 67 that changes in size as the iris diaphragm 69 is changed. Diaphragm 69 is controlled by pin 71 mounted in ring gear 75. Clockwise movement of ring gear 75 opens aperture 67 while counterclockwise movement of ring gear 75 closes diaphragm 69 and therefore aperture 67. FIG. 5 illustrates how ring gear 75 is mounted by bearings 77 on flange 79, with iris 65 also being mounted on flange 79. Flange 79 is pinned to iris retaining ring 83 by pin 81, with iris 65 contained inside retaining ring 83. Large centrally located machine screw 85 locks retaining ring 83 into vertically upstanding housing block 87 also shown in FIG. 5, is the pin 71 extending through arcuate slot 73 in flange 79 to iris 65. The iris actuating ring gear 75 is driven, upon command from the control board as previously described, by second or iris motor 45, which drives spur gear 89 on shaft 91 of motor 45. The movement of the iris diaphragm 69 is the first axis of motion for the present invention, illustrated by arrows 93 in FIG. 4.

Figure 2:
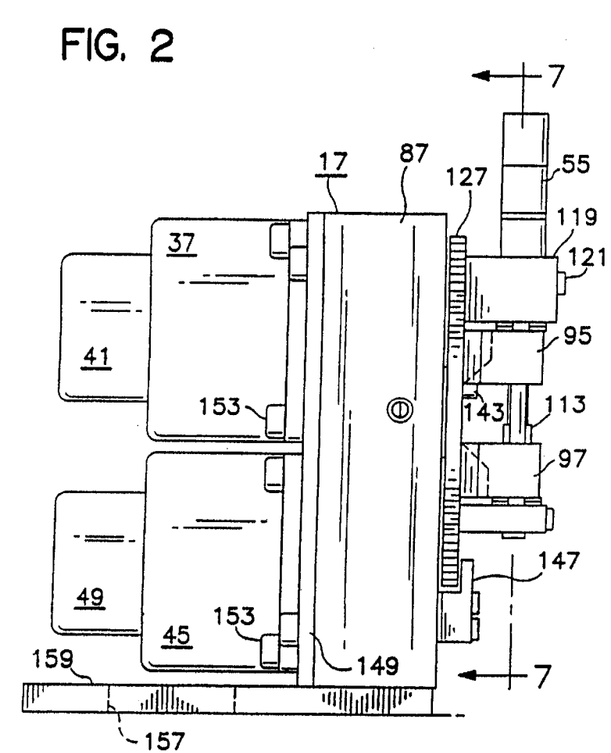
FIG. 2 is an enlarged, side elevational view of the device shown in FIG. 1.
Figure 7:
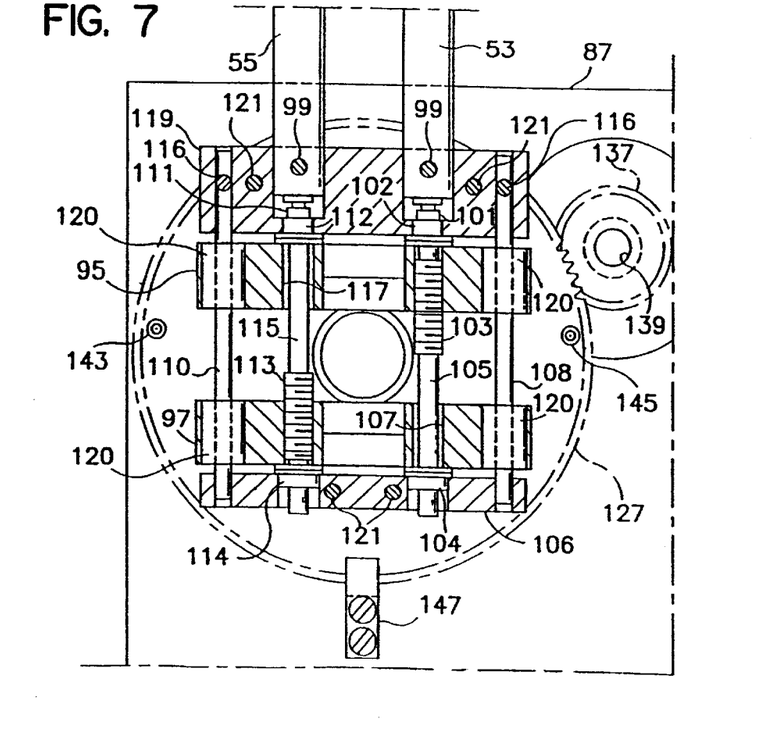
FIG. 7 is an enlarged, fragmentary, sectional view taken on the line 7,7 of FIG. 2 showing additional details of the drive mechanisms for the doors and the gear drive for the rotational position of the door assembly.

On the right hand side of the device 17 shown in FIG. 2, also known as the back or exit side, are a pair of door sections 95 and 97 respectively. FIG. 7 illustrates the manner in which upper door section 95 is driven by motor 53 and associated screw shaft 101, which shaft is in turn threaded into door section 95 by screw portion 103. The lower terminal end 105 of shaft 101 passes through clearance passage 107 in lower door section 97.

Motor mounting block 119 mounts the two motors 53 and 55 such that they are secured in bores in block 119 by means of set screws 99. The output shafts of the motors 53 and 55 are attached into the upper terminal ends of two screw shafts 101 and 111, respectively. The screw shafts 101 and 111 are mounted respectively in bearings 102 and 112 in the lower face of block 119. The lower terminal ends of screw shafts 101 and 111 are carried in bearings 104 and 114, respectively, in the lower mounting block 106. The upper door 95 threadedly engages with the threaded portion 103 of screw shaft 101 and is driven up or down by motor 53. The lower door section 97 threadedly engages with the threaded portion 113 of screw shaft 111 and is driven up or down by means of motor 55.

The two door sections 95 and 97 are stabilized for up and down motion using two guide rods 108 and 110 that extend between upper block 119 and the lower mounting block 106. The guide rods 108 and 110 are secured from movement by means of set screws 116 in the upper block 119. The two door sections 95 and 97 each have linear bearings 120 mounted on their outer ends to engage with the guide rods 108 and 110. The entire door assembly is mounted to the face of gear 127 by means of two screws 121 in the upper block 119 and two similar screws 121 in the lower mounting block 106.

Similarly, motor 55 and associated screw shaft 111 activates door section 97 by screw portion 113 such that the upper end 115 of shaft 111 has clearance for upper door section 95 through clearance passage 117.

Figure 3:
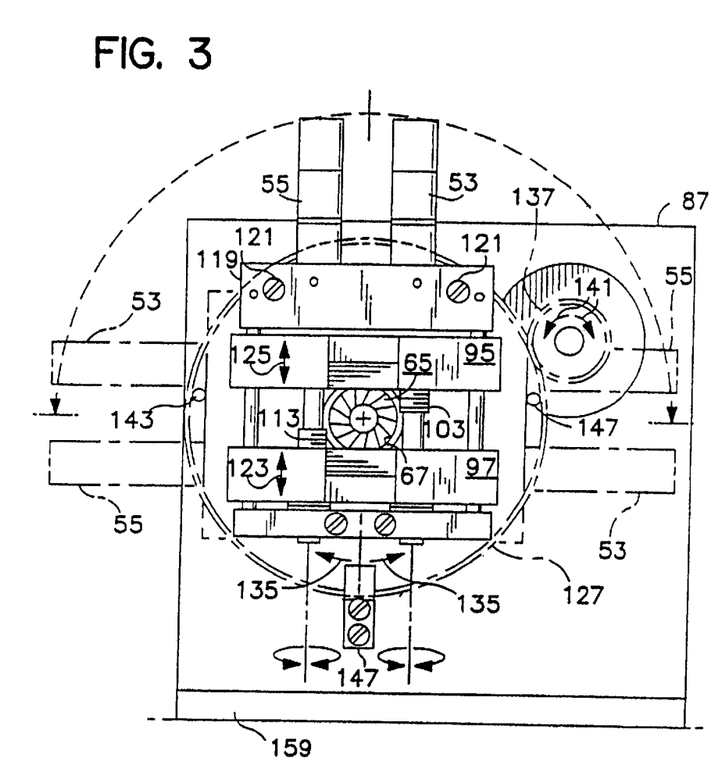
FIG. 3 is a rear or right hand elevational view of FIG. 2.

Motor mounting block 119 mounts motors 53 and 55 which in turn move door sections 95 and 97 respectively in the direction shown by arrows 123 and 125 in FIG. 3, for example, so as to restrict a laser beam passing through aperture 67 along axis 15.

In the preferred embodiment shown herein, door section 95 is moved by motor 53 independent of whether or not door section 97 is moved by motor 55, and, of course, the reverse is true as well since both motors 53 and 55 are controlled and activated separately, depending upon the predetermined pattern. Thus one side or the other of the laser beam pulse may be larger or smaller than the other side as desired.

The entire door means including motors 53 and 55 are mounted on the motor mounting block 119, which block 119 is attached to a ring gear 127 by screws 121. Ring gear 127 is mounted on bearings 129, in turn mounted on flange 131. Flange 131 is attached by machine screws 133 to housing block 87. FIG. 3 illustrates the final axis of movement of the sculpturing device 17. Ring gear 127 moves in the direction of arrow 135 by spur gear 137 on drive shaft 139 of motor 37. Motor 37 rotates shaft 139 and spur gear 137 in the direction of arrow 141, rotating ring gear 127 about axis 15 by 180 degrees in both the clockwise and counterclockwise directions. Machine limit screws 143 and 145 limit travel to 180 degrees upon contact with limit stop 147 at the bottom of block housing 87. The device shown in FIG. 7 is limited to approximately but not less than 180 degrees of movement in each direction but other limits are possible as desired. It may be possible to travel a full 360 degrees with a different assembly.

At every position, encoder 41 provides feedback to the controller as to the angular position of rotation about axis 15 in the direction of arrow 135. Similarly, encoder 49 provides feedback to the controller as to the angular position of iris diaphragm 69, and thus the size of aperture 67. Motors 53 and 55 are also provided internal encoders at the top thereof to provide feedback as to the position of door sections 95 and 97 by signaling the position of screw 103 in door section 95 and screw 113 in door section 97.

The sculpturing device 17 may be adjusted or serviced by removal of angularly shaped closure plate 149. Motors 37 and 41 are mounted to housing block 87 via machine screws 153. Screws 153 serve also to hold closure plate 149 in place as it rests on ledge 155, covering the mechanisms inside housing block 87, leaving a space between closure plate 149 and ring gear 75 as shown in FIG. 5. The shape of closure plate 149 is shown in FIG. 4 where the left side of closure plate 149 is in dash line in part to show the location of motors 37 and 41, among other things.

Figure 6:
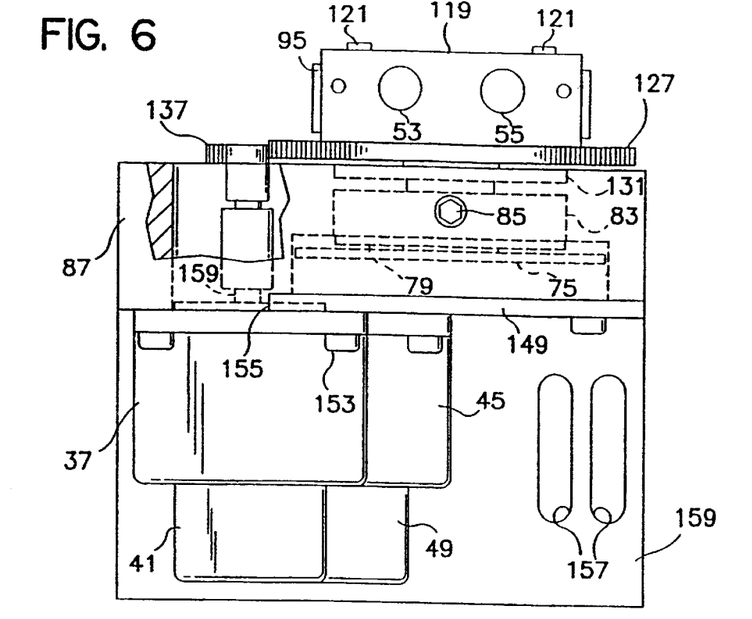
FIG. 6 is a plan view of FIG. 4 showing the drive mechanism for the angular disposition of the door and slot mechanism.

FIG. 6 is a top plan view illustrating the slots 157 in base plate 159 which permit precise mounting and location of the entire sculpturing device 17 on table 25 so that it may be properly oriented with respect to a laser 11 and the other components illustrated in FIG. 1.

THE METHODS

In addition to the devices and systems described above, the present invention provides methods which have great utility in the treatment of malfunctions of the optical organs in animals, particularly the corneas of humans. For example, it can now be seen that the sculpturing device 17 can be operated to restrict the laser beam traveling along laser beam axis 15 in four ways. First, the aperture 67, which can be enlarged or made smaller by iris diaphragm 69, circumferentially restricts the laser beam, such as for use in certain treatment such as myopia. Also, block sections 95 and 97 may be moved, independently in this embodiment, to further restrict the laser beam on one side or both sides as the predetermined pattern requires for second and third axes of restriction. Finally, the entire assembly may be rotated about the fourth axis, which is the laser beam axis, so that either door section 95 or 97, or both door sections, may restrict a different portion of the laser beam.

Figure 8:
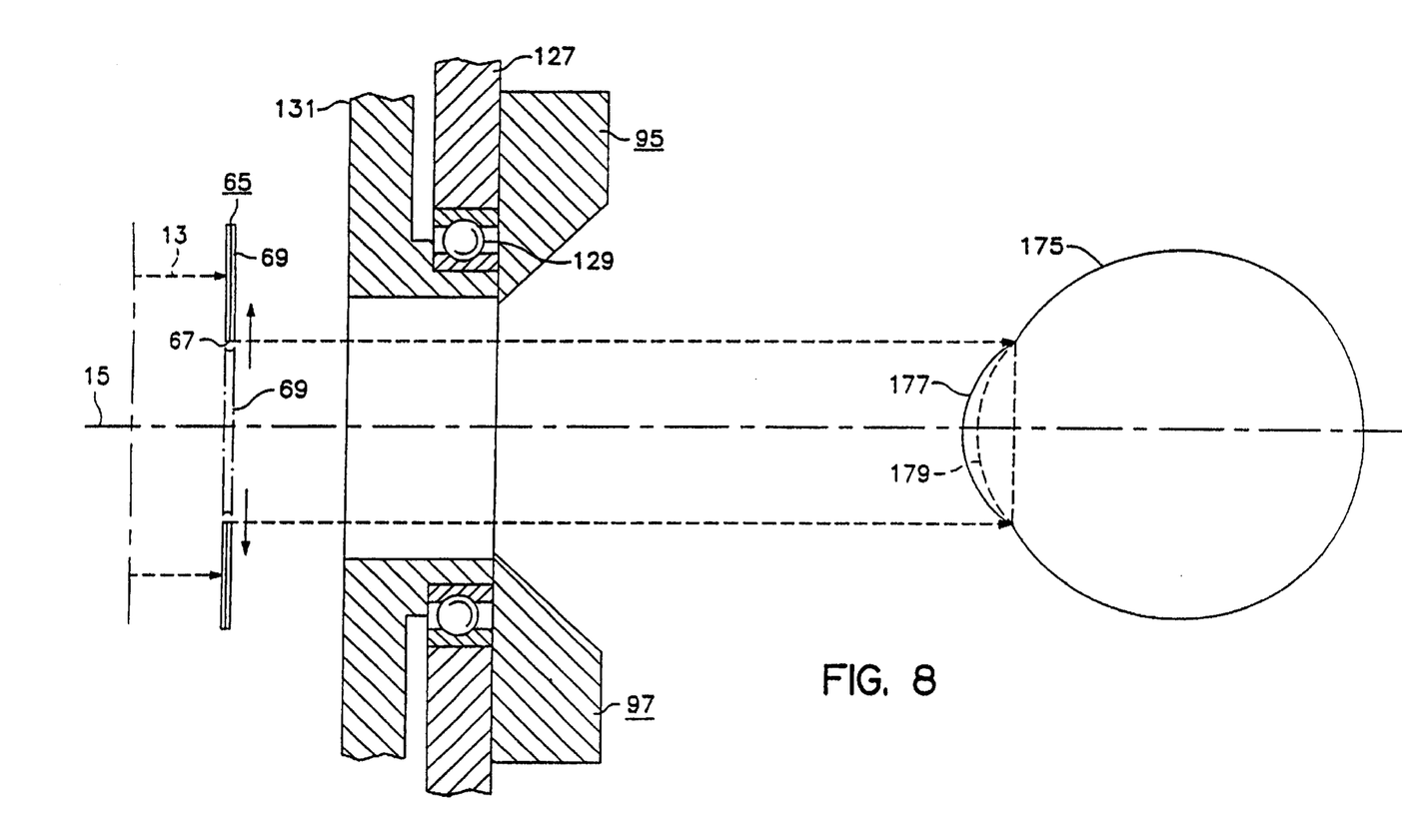
FIG. 8 is an enlarged, schematic view showing the general arrangement of the system of this invention for a surgical procedure on the eye to correct myopia.

As noted above, the present invention is admirably suited for use in eye surgery, and more particularly to treatment of the eye to correct astigmatism, myopia, or hyperopia. FIG. 8 illustrates the general arrangement of the device 17 as the laser beam 13 passes along axis 15, from left to right in the drawing, to first impact on diaphragm 69 of iris 65 and pass through that portion of the laser beam pulse that fits within aperture 67. The laser beam pulse is not restricted by door sections 95 and 97, shown in position next to ring gear 127, in turn supported as previously described on bearing 129 on flange 131. Eye 175 and cornea 177 are treated for myopia by the system in this configuration. The door sections 95 and 97 are fully open and the iris diaphragm 69 is fully closed. The laser is then pulsed one or more times at various predetermined settings as the iris is opened at predetermined increments. The dotted line 179 illustrates the flattened cornea after treatment.

Figure 9:
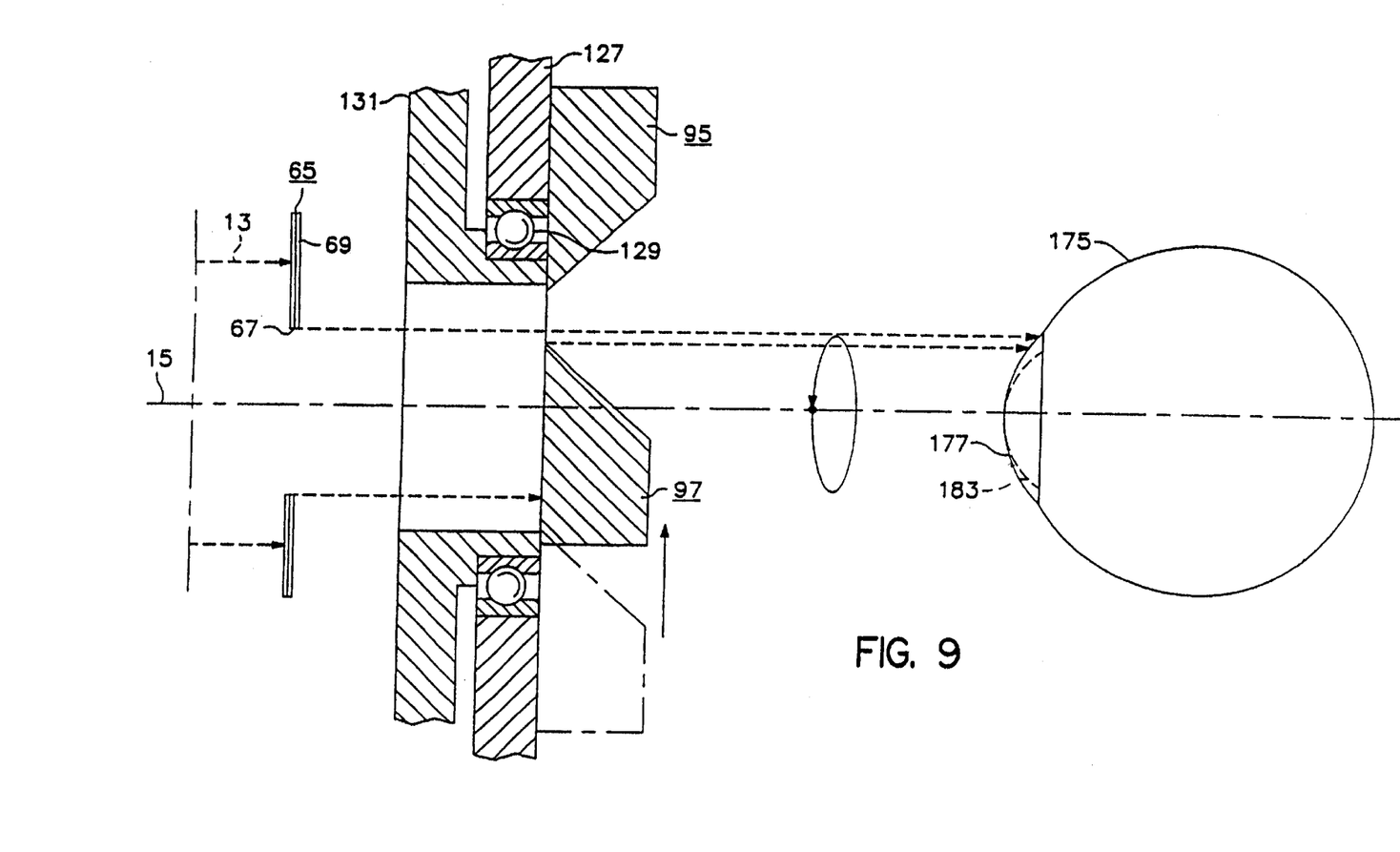
FIG. 9 is a view similar to FIG. 8 for a surgical procedure to correct hyperopia.

FIG. 9 illustrates a the configuration of the present so as treatment for hyperopia in which the aperture 67 is open to a predetermined diameter. According to preferred methods of present invention, the cornea 175 is exposed to a plurality of asymmetrical laser beam subportions to affect a substantially symmetrical correction in the shape of the cornea. According to a preferred embodiment, the upper door section 95 is open to its maximum spacing and lower door section 97 is raised to a chordal cutting position to exclude a large portion of the laser beam pulse and thereby create a laser beam subportion that is asymmetrical about the laser axis. A plurality of corneal regions can then be exposed to a plurality of laser beam subportions by: rotating the door portions about the laser axis and exposing the cornea to radiation at a plurality of such indexed positions; and/or occluding a smaller portion of the laser beam by opening door portion 97 and exposing the cornea to radiation at a plurality of such positions. The procedure may thus be used to achieve the results 183 on the cornea 177 to produce hyperopic treatment.

FIGS. 11–16 provide a diagrammatic view of the operation of preferred embodiments of the present methods. FIGS. 11a–11f illustrate shape of a laser beam after successive exposures to a cornea according to on embodiment of the present invention. In these figures, the predefined cross sectional shape of the laser beam 200 is circular, as represented by FIG. 11a. It will be appreciated, of course, that all varieties of predefined shapes are adaptable for use in accordance with the present invention. The first exposure of the cornea includes occluding the beam to produce a beam subportion having a configuration 201 as shown in FIG. 11b to produce a segment of the circle that defined the original predefined shape. According to one embodiment, the second, third, fourth and fifth exposure of the cornea includes occluding the beam to produce a plurality of beam subportions having the configurations 202–205 shown in FIGS. 11c–11f. Such a plurality of beam subportions can be readily achieved by the device of FIG. 9 by rotating the doors through a series of predefined angles. In general, it is preferred and contemplated that the present methods include the increasing the size of the laser beam subportions and reexposing the cornea to a plurality of such beam subportions, as shown in FIGS. 12b–12f.

It will be readily apparent to those skilled in the art that numerous variations on the illustrated embodiments are available within the scope of the present invention. For example, although the beam subportions in FIGS. 11a–11f are shown as to not substantially overlap, this is certainly not required, and in fact it is contemplated that each beam subportion may include a portion of a previous or subsequent beam subportion, as is the case in FIGS. 12b–12f. Furthermore, the size and relative angle of rotation of the subsequent beam subportions can be the same or different, depending upon the desired result. It will be appreciated by those skilled in the art, however, that the present methods are adaptable to effectively and efficiently treat hyperopia by utilizing a plurality of asymmetrical beam subportions to produce a change in cornea shape without introducing any substantial asymmetry to the cornea.

Figure 13A:
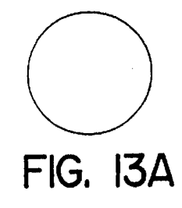
FIGS. 13A–13F are diagrammatic views of the operation according to an embodiment of the invention involving the use of overlapping subportions, having substantially parallel chords.
Figure 13B:
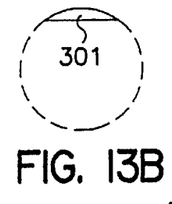
Figure 13C:
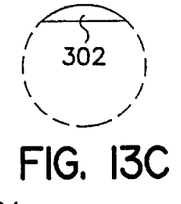
Figure 13D:
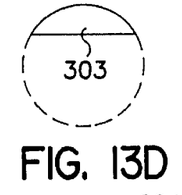
Figure 13E:
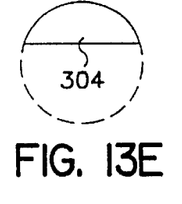
Figure 13F:
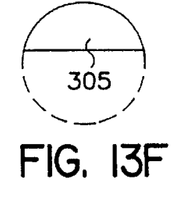

FIGS. 13a–13f provide a diagrammatic view of the operation of another preferred embodiment of the present methods. In these figures, the predefined cross sectional shape of the laser beam 300 is also circular, as represented by FIG. 13a, it being once again appreciated that all varieties of predefined shapes are adaptable for use. The first exposure of the cornea includes occluding the beam to produce a beam subportion having a configuration 301 as shown in FIG. 13b to produce a segment of the circle that defined the original predefined shape. According to one embodiment, the second, third, fourth and fifth exposure of the cornea includes occluding the beam to produce a plurality of beam subportions having the configurations 302–305 shown in FIGS. 13c–13f. Such a plurality of beam subportions can be readily achieved by the device of FIG. 9 by simply incrementing the opening of the doors in the device shown in FIG. 10. According to a preferred embodiment, after being exposed to the laser beam subportions as illustrated in FIG. 13b–13f, the doors are indexed 90 degrees about the axis of the laser beam and the exposure treatment is repeated with the doors creating a series of laser beam subportions 401–405 with the doors rotated to this position. All exposures in this 90 degree rotation are shown in compressed form in FIG. 14. The operation is then repeated with the doors at 180 degrees to produce subportions 501–505 and at 270 degrees to produce subportions 601–605, as shown in compressed form in FIGS. 15 and 16.

Figure 14:
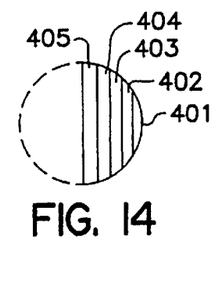
Figure 15:
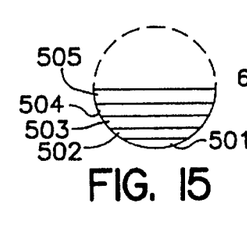
FIGS. 15–16 are diagrammatic views of the exposures in a 180° rotation in compressed form.
Figure 16:
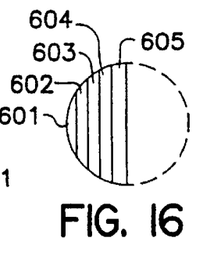

In preferred embodiments of the methods illustrated in FIGS. 13–15, the diameter of the predefined laser beam is about 8 mm and the steps illustrated in FIGS. 13b–13f comprising opening the doors about 40 times in 0.1 mm increments until the laser beam is substantially bisected to produce a semi-circular subportion. This procedure is then repeated for each of the quadrants illustrated in FIGS. 14–16.

Figures 10, 11:
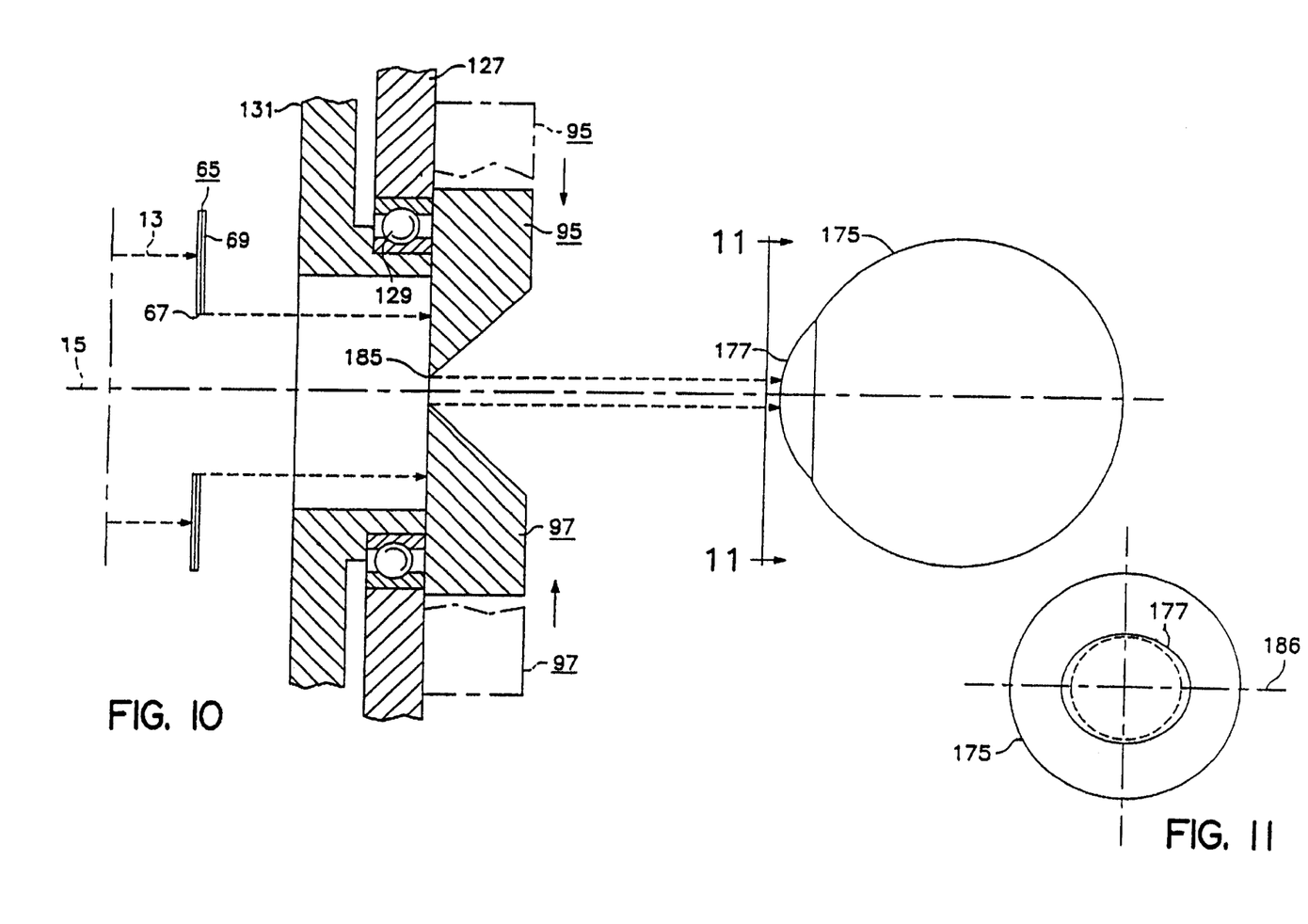
FIG. 10 is a is view similar to FIGS. 8 and 9 for astigmatism.
FIG. 11 is front view, at reduced scale, showing the major axis of an elliptical shaped cornea.
Figure 11A:
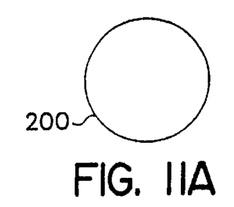
FIGS. 11A–11F are diagrammatic cross-sectional views illustrating the occluded shape of a laser beam in accordance to the present invention.
Figure 11B:
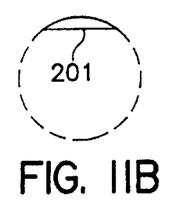
Figure 11C:
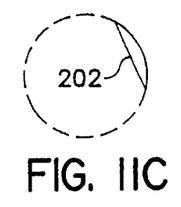
Figure 11D:
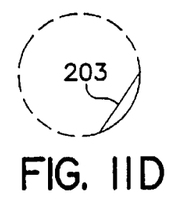
Figure 11E:
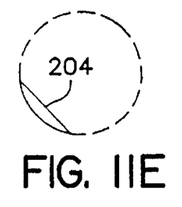
Figure 11F:
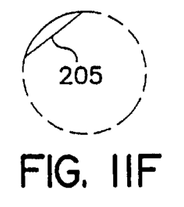
Figure 12A:
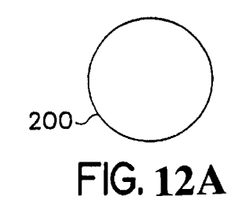
FIGS. 12A–12F are diagrammatic views of the operation illustrating embodiments of the invention involving increasing the size of the laser beam subportions and reexposing the cornea.
Figure 12B:
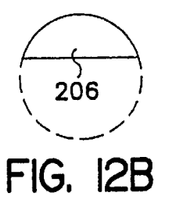
Figure 12C:
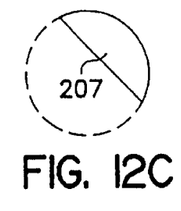
Figure 12D:
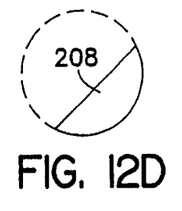
Figure 12E:
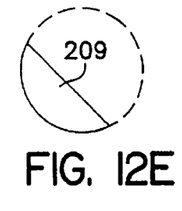
Figure 12F:
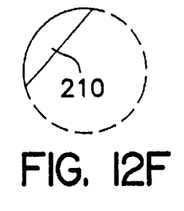

FIG. 10 illustrates a treatment condition for astigmatism in which both upper door section 95 and lower door section 97 converge to a nearly closed position, as shown, to form a thin slit. In this procedure, the door assembly is not rotated other than initially when aligning the slit band 185 to the major axis 186 of the elliptically shaped cornea. Again, this procedure is repeated over varying predetermined increments of slit band width to achieve results 190 on cornea 177.

As will become apparent from reading the foregoing, the doors and iris of the sculpturing device of this invention may be manipulated to project a wide variety of laser beam patterns on a target such as, for example, the human eye. Such patterns include, by way of example and not of limitation, annuli of varying sizes, segments, ellipses, ovals and other curved shapes. Also, use of the door sections along the entire periphery of the beam, in sequential steps, permits projection of straight edged shapes such as rectangles and the like.

While particular embodiments of the present invention have been illustrated and described, it is not intended to limit the invention. Other embodiments, forms and modifications of the invention coming within the scope and spirit of the appended claims will, of course, readily suggest themselves to those skilled in the art.

What is claimed is:

1. A method of applying a beam of tissue-ablating laser radiation to affect the shape of a cornea without introducing any substantial asymmetry to the shape of said cornea, said method comprising the steps of exposing the cornea to laser radiation comprising the steps of:

(a) providing a laser beam having an predefined shape along a beam axis; and (b) exposing a plurality of corneal regions to a plurality of laser beam subportions to affect the shape of said cornea without introducing any substantial asymmetry to the shape of said cornea, said laser beam subportions each being asymmetrical with respect to said laser beam axis and having a cross sectional shape substantially defined by a portion of the periphery of said predefined shape, each of said subportions of said laser beam being produced by occluding a portion of said beam of predefined shape.

2. A method of applying a beam of tissue-ablating laser radiation to affect the shape of a cornea, said method comprising the steps of exposing the cornea to laser radiation comprising the steps of providing a laser beam having an predefined shape along a beam axis and sequentially:

(a) exposing a series of successive first region of the cornea to a first subportion of said laser beam, said first subportion of the beam being asymmetrical with respect to said laser beam axis and having a cross sectional shape substantially defined by a portion of the periphery of said predefined shape, said subportion of said laser beam being produced by occluding a portion of the beam of predefined shape; and (b) exposing at least a second region of the cornea to a second subportion of said laser beam, said second subportion of the beam being asymmetrical with respect to said laser beam axis and having a cross sectional shape substantially defined by a portion of the periphery of said predefined shape, said subportion of said laser beam being produced by occluding a portion of the beam of predefined shape; a segmental shape consisting of a base and an arc wherein at least a portion of the arc of the second portion of the beam is coincident with the arc of the first portion of the beam and wherein said second portion of the beam is larger than said first portion of the beam and includes all of said first portion of the beam, said second portion of the beam being produced by occluding the beam;

(b) exposing a second region of the cornea to laser radiation wherein said second region is complementary to the first region of the cornea comprising the steps of sequentially:

(i) exposing a first part of the second region of the cornea to a third portion of said beam, said third portion of the beam having a segmental shape consisting of a base and an arc and being produced by occluding the beam; and (ii) exposing at least a second part of the second region of the cornea to a fourth portion of said beam, said fourth portion of the beam having a segmental shape consisting of a base and an arc wherein at least a portion of the arc of the fourth portion of the beam is coincident with the arc of the third portion of the beam and wherein said fourth portion of the beam is larger than said third portion of the beam and includes all of said third portion of the beam, said fourth portion of the beam being produced by occluding the beam;

(c) exposing a third region of the cornea to laser radiation comprising the steps of sequentially:

(i) exposing a first part of the third region of the cornea to a fifth portion of said beam, said fifth portion of the beam having a segmental shape consisting of a base and an arc wherein a line coincident with the base of said fifth portion of the beam is perpendicular to a line coincident with the base of said first portion of the beam, said fifth portion being produced by occluding the beam; and (ii) exposing at least a second part of the third region of the cornea to a sixth portion of said beam, said sixth portion having a segmental shape consisting of a base and an arc wherein at least a portion of the arc of the sixth portion of the beam is coincident with the arc of the fifth portion of the beam and wherein said sixth portion of the beam is larger than said fifth portion of the beam and includes all of said fifth portion of the beam, said sixth portion of the beam being produced by occluding the beam; and (d) exposing a fourth region of the cornea to laser radiation wherein said fourth region is complementary to the third region of the cornea comprising the steps of sequentially:

(i) exposing a first part of the fourth region of the cornea to a seventh portion of said beam, said seventh portion of the beam having a segmental shape consisting of a base and an arc and being produced by occluding the beam; and (ii) exposing at least a second part of the fourth region of the cornea to an eighth portion of said beam, said eighth portion of the beam having a segmental shape consisting of a base and an arc wherein at least a portion of the arc of the eighth portion of the beam is coincident with the arc of the seventh portion of the beam and wherein said eight portion of the beam is larger than said seventh portion of the beam and includes all of said seventh portion of the beam, said eighth portion of the beam being produced by occluding the beam.

3. A method of applying a beam of tissue-ablating laser radiation to affect the shape of a cornea, said method comprising the steps of:

(a) exposing a first region of the cornea to laser radiation comprising the steps of sequentially:

(i) exposing a first part of the first region of the cornea to a first portion of a laser beam, said beam having a substantially circular cross-section, said first portion of the beam having a segmental shape consisting of a base and an arc and being produced by occluding the beam; and (ii) exposing at least a second part of the first region of the cornea to a second portion of said beam, said second portion of the beam having a segmental shape consisting of a base and an arc wherein at least a portion of the arc of the second portion of the beam is coincident with the arc of the first portion of the beam and wherein said second portion of the beam is larger than said first portion of the beam and includes all of said first portion of the beam, said second portion of the beam being produced by occluding the beam; and (b) exposing at least a second region of the cornea to laser radiation comprising the steps of sequentially:

(i) exposing a first part of at least the second region of the cornea to a third portion of said beam, said third portion of the beam having a segmental shape consisting of a base and an arc wherein said base of said third portion is oriented angularly to said base of said first portion of the beam, said third portion of the beam being produced by occluding the beam; and (ii) exposing at least a second part of at least the second region of the cornea to a fourth portion of said beam, said fourth portion of the beam having a segmental shape consisting of a base and an arc wherein at least a portion of the arc of the fourth portion of the beam is coincident with the arc of the third portion of the beam and wherein said fourth portion of the beam is larger than said third portion of the beam and includes all of said third portion of the beam, said fourth portion of the beam being produced by occluding the beam.

4. A method of applying a beam of tissue-ablating laser radiation to affect the shape of a cornea, said method comprising the steps of:

(a) exposing a first region of the cornea to laser radiation comprising the steps of sequentially:
(i) exposing a first part of the first region of the cornea to a first portion of a laser beam said first portion of the beam being produced by occluding the beam; and
(ii) exposing at least a second part of the first region of the cornea to a second portion of said beam wherein said second portion of the beam is larger than said first portion of the beam and includes all of said first portion of the beam, said second portion of the beam being produced by occluding the beam; and (b) exposing at least a second region of the cornea to laser radiation comprising the steps of sequentially:
(i) exposing a first part of at least the second region of the cornea to a third portion of said beam, said third portion of the beam being produced by occluding the beam; and
(ii) exposing at least a second part of the second region of the cornea to a second portion of said beam wherein said second portion of the beam is larger than said first portion of the beam and includes all of said first portion of the beam, said second portion of the beam being produced by occluding the beam.

5. A method of applying a beam of tissue-ablating laser radiation to affect the shape of a cornea, said method comprising the steps of:

(a) exposing a first region of the cornea to laser radiation comprising the steps of sequentially:
(i) exposing a first part of the first region of the cornea to a first portion of a laser beam, said beam having a substantially circular cross-section, said first portion of the beam having a segmental shape consisting of a base and an arc and being produced by occluding the beam; and
(ii) exposing at least a second part of the first region of the cornea to a second portion of said beam, said second portion of the beam having a segmental shape consisting of a base and an arc wherein the base of the second portion of the beam is spaced from and parallel to the base of the first portion of the beam and wherein said second portion of the beam is larger than said first portion of the beam and includes all of said first portion of the beam, said second portion of the beam being produced by occluding the beam;

(b) exposing a second region of the cornea to laser radiation wherein said second region is complementary to the first region of the cornea comprising the steps of sequentially:
(i) exposing a first part of the second region of the cornea to a third portion of said beam, said third portion of the beam having a segmental shape consisting of a base and an arc and being produced by occluding the beam; and
(ii) exposing at least a second part of the second region of the cornea to a fourth portion of said beam, said fourth portion of the beam having a segmental shape consisting of a base and an arc wherein the base of the fourth portion of the beam is spaced from and parallel to the base of the third portion of the beam and wherein said fourth portion of the beam is larger than said third portion of the beam and includes all of said third portion of the beam, said fourth portion of the beam being produced by occluding the beam;

(c) exposing a third region of the cornea to laser radiation comprising the steps of sequentially:
(i) exposing a first part of the third region of the cornea to a fifth portion of said beam, said fifth portion of the beam having a segmental shape consisting of a base and an arc wherein a line coincident with the base of said fifth portion of the beam is perpendicular to a line coincident with the base of said first portion of the beam, said fifth portion being produced by occluding the beam; and
(ii) exposing at least a second part of the third region of the cornea to a sixth portion of said beam, said sixth portion of the beam having a segmental shape consisting of a base and an arc wherein the base of the sixth portion of the beam is spaced from and parallel to the base of the fifth portion of the beam and wherein said sixth portion of the beam is larger than said fifth portion of the beam and includes all of said fifth portion of the beam, said sixth portion of the beam being produced by occluding the beam; and (d) exposing a fourth region of the cornea to laser radiation wherein said fourth region is complementary to the third region of the cornea comprising the steps of sequentially:
(i) exposing a first part of the fourth region of the cornea to a seventh portion of said beam, said seventh portion of the beam having a segmental shape consisting of a base and an arc and being produced by occluding the beam; and
(ii) exposing at least a second part of the fourth region of the cornea to an eighth portion of said beam, said eighth portion of the beam having a segmental shape consisting of a base and an arc wherein the base of the eighth portion of the beam is spaced from and parallel to the base of the seventh portion of the beam and wherein said eight portion of the beam is larger than said seventh portion of the beam and includes all of said seventh portion of the beam, said eighth portion of the beam being produced by occluding the beam.

* * * * *